United States Patent
Bates et al.

(10) Patent No.: US 9,286,914 B2
(45) Date of Patent: Mar. 15, 2016

(54) CARTRIDGE FOR STORING BIOSAMPLE CAPILLARY TUBES AND USE IN AUTOMATED DATA STORAGE SYSTEMS

(75) Inventors: Allen Keith Bates, Tucson, AZ (US); Nils Haustein, Soergenloch (DE); James William Johnson, Tucson, AZ (US); Thorsten Krause, Mainz (DE); Stephen Leonard Schwartz, Tucson, AZ (US); Anna Wanda Topol, Jefferson Valley, NY (US); Ulf Troppens, Mainz (DE); Daniel James Winarski, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 947 days.

(21) Appl. No.: 13/151,247

(22) Filed: Jun. 1, 2011

(65) Prior Publication Data

US 2012/0309297 A1    Dec. 6, 2012

(51) Int. Cl.
*C40B 60/04* (2006.01)
*G11B 5/008* (2006.01)
(Continued)

(52) U.S. Cl.
CPC ........ *G11B 5/00821* (2013.01); *A61B 10/0096* (2013.01); *B01L 9/065* (2013.01); *G11B 23/049* (2013.01); *A61B 5/150305* (2013.01); *B01L 2300/0809* (2013.01);
(Continued)

(58) Field of Classification Search
CPC ....... B01L 9/06; B01L 3/508; B01L 3/50855; B01L 9/00; B01L 3/502; B01L 3/502738; B01L 9/065; B01L 2300/0809; B01L 2300/0812; G01N 35/00029; G01N 35/025; G01N 21/03; G01N 35/026; G01N 2035/0425; G01N 35/0099; A61B 5/14532; A61B 5/1427; A61B 5/1438; A61B 10/0283; A61B 10/0096; A61B 5/150305; G11B 25/066; G11B 23/087; G11B 15/07; G11B 15/675; G11B 15/67549; G11B 25/063; G11B 23/07; G11B 5/00821; G11B 23/049; B01J 19/0046; B82Y 30/00; C40B 60/14; C40B 60/10; C40B 60/12
USPC ......... 422/561, 562, 565; 360/94, 93; 506/33, 506/35; 235/492, 493, 487; 455/39; 398/118; 414/331.01; G9B/5.002, G9B/5.024
See application file for complete search history.

(56) References Cited

U.S. PATENT DOCUMENTS 3,859,624 A   1/1975   Kriofsky et al.
4,650,981 A   3/1987   Foletta
(Continued)

OTHER PUBLICATIONS

R. Davies et al., "Engineered Particle Surfaces," Advanced Materials, vol. 10, No. 15, pp. 1264-1270, Published Online: Jan. 26, 1999.
(Continued)

*Primary Examiner* — Glenn Myers
(74) *Attorney, Agent, or Firm* — Zilka-Kotab, PC

(57) ABSTRACT

Embodiments of the disclosure relate to a cartridge that includes slots for storing biosample capillary tubes. The cartridge has the same form factor as data tape cartridges to allow the cartridge to be handled by the same robotic mechanisms that handle data cartridges in an automated tape library. One aspect of the disclosure concerns a cartridge comprising an enclosure that includes a movable door to provide access to a tube holder in the enclosure. The tube holder includes cylindrical holes or slots for receiving capillary tubes which contain biosamples scanned and analyzed an automated tape library.

19 Claims, 9 Drawing Sheets

(51) Int. Cl.
*A61B 10/00* (2006.01)
*G11B 23/04* (2006.01)
*B01L 9/06* (2006.01)
*A61B 5/15* (2006.01)
*G01N 35/00* (2006.01)
*G01N 35/04* (2006.01)

(52) U.S. Cl.
CPC .. *B01L 2300/0812* (2013.01); *G01N 35/00029* (2013.01); *G01N 35/0099* (2013.01); *G01N 2035/0425* (2013.01)

(56) References Cited

U.S. PATENT DOCUMENTS

| | | | |
|---|---|---|---|
| 4,758,836 A | 7/1988 | Scuilli | |
| 4,941,201 A | 7/1990 | Davis | |
| 5,320,808 A | 6/1994 | Holen et al. | |
| 6,201,474 B1 | 3/2001 | Brady et al. | |
| 6,429,016 B1 | 8/2002 | McNeil | |
| 6,637,473 B2 | 10/2003 | Ganz et al. | |
| 6,699,437 B1 | 3/2004 | Astle | |
| 6,875,405 B1* | 4/2005 | Mathus et al. | 422/562 |
| 7,118,708 B2 | 10/2006 | Mordekhay | |
| 7,142,987 B2 | 11/2006 | Eggers | |
| 7,382,258 B2* | 6/2008 | Oldham et al. | 340/572.1 |
| 7,596,251 B2 | 9/2009 | Affleck et al. | |
| 7,635,246 B2 | 12/2009 | Neeper et al. | |
| 7,660,063 B2 | 2/2010 | Bates et al. | |
| 7,663,487 B2* | 2/2010 | Morris et al. | 340/572.1 |
| 7,670,553 B2 | 3/2010 | Babson | |
| 7,922,986 B2* | 4/2011 | Byrnard et al. | 422/561 |
| 7,988,644 B2 | 8/2011 | Freeman et al. | |
| 7,997,682 B2 | 8/2011 | Silverbrook | |
| 8,012,745 B2 | 9/2011 | Glezer et al. | |
| 8,337,785 B2* | 12/2012 | Davies et al. | 422/553 |
| 8,640,964 B2 | 2/2014 | Bates et al. | |
| 9,207,229 B2 | 12/2015 | Bates et al. | |
| 2003/0039591 A1* | 2/2003 | Pham et al. | 422/102 |
| 2003/0087454 A1 | 5/2003 | Schultz et al. | |
| 2005/0180894 A1 | 8/2005 | Petroff et al. | |
| 2006/0161935 A1* | 7/2006 | Johnson et al. | 720/645 |
| 2009/0117011 A1 | 5/2009 | Morrison | |
| 2010/0105074 A1 | 4/2010 | Covey et al. | |
| 2011/0076670 A1 | 3/2011 | Boday et al. | |
| 2012/0309298 A1 | 12/2012 | Bates et al. | |
| 2014/0018265 A1 | 1/2014 | Bates et al. | |
| 2014/0094114 A1 | 4/2014 | Bates et al. | |

OTHER PUBLICATIONS

Non-Final Office Action from U.S. Appl. No. 13/151,249, dated Feb. 4, 2013.
Final Office Action from U.S. Appl. No. 13/151,249, dated Jul. 17, 2013.
Notice of Allowance from U.S. Appl. No. 13/151,249, dated Sep. 20, 2013.
Non-Final Office Action from U.S. Appl. No. 14/029,667, dated Nov. 15, 2013.
Letter Restarting Period for Response from U.S. Appl. No. 14/029,667, dated Dec. 19, 2013.
Non-Final Office Action from U.S. Appl. No. 14/029,667, dated Jun. 4, 2014.
Final Office Action from U.S. Appl. No. 14/029,667, dated Nov. 19, 2014.
Advisory Action from U.S. Appl. No. 14/029,667, dated Feb. 12, 2015.
Notice of Allowance from U.S. Appl. No. 14/029,667, dated Mar. 30, 2015.
Non-Final Office Action from U.S. Appl. No. 13/632,021, dated Feb. 13, 2015.
ECMA, "Standardizing Information and Communication Systems: Data Interchange on 12,7 mm 384-Track Magnetic Tape Cartridges—Ultrium-1 Format," Standard ECMA-319, Jun. 2001, 13 pages.
Bates et al., U.S. Appl. No. 14/029,667, filed Sep. 17, 2013.
Bates et al., U.S. Appl. No. 13/632,021, filed Sep. 30, 2012.
Bates et al., U.S. Appl. No. 13/151,249, filed Jun. 1, 2011.
Boday et al., U.S. Appl. No. 12/888,388, filed Sep. 22, 2010.
Final Office Action from U.S. Appl. No. 13/632,021, dated Aug. 25, 2015.
Notice of Allowance from U.S. Appl. No. 14/029,667, dated Jul. 29, 2015.
Notice of Allowance from U.S. Appl. No. 13/632,021, dated Sep. 30, 2015.
Bates et al., U.S. Appl. No. 14/929,082, filed Oct. 30, 2015.
Supplemental Notice of Allowance from U.S. Appl. No. 13/632,021, dated Dec. 1, 2015.
Non-Final Office Action from U.S. Appl. No. 14/929,082, dated Dec. 2, 2015.
Supplemental Notice of Allowance from U.S. Appl. No. 13/632,021, dated Dec. 16, 2015.
Bates et al., U.S. Appl. No. 14/981,791, filed Dec. 28, 2015.

* cited by examiner

CARTRIDGE FOR STORING BIOSAMPLE CAPILLARY TUBES AND USE IN AUTOMATED DATA STORAGE SYSTEMS

CROSS-REFERENCE TO RELATED APPLICATIONS

This application is related to concurrently filed and commonly-assigned U.S. patent application Ser. No. 13/151,249, entitled "A Cartridge For Storing Biosample Plates And Use In Automated Data Storage Systems", now U.S. Pat. No. 8,640,964, which is hereby incorporated by reference.

FIELD OF THE INVENTION

Embodiments of the invention relate to analytical devices and systems, and more particularly, to a cartridge for holding biosample capillary tubes wherein the cartridge may be stored in the cartridge storage slots of tape library systems and handled by the robotic mechanisms of the tape library systems.

BACKGROUND

Samples of biological matters are often analyzed in bioassay processes to detect the presence of bacteria, viruses, cancer cells, and other substances of interest. The biosamples may be stored in capillary tubes and analyzed by a biological detection instrument. The detection instrument may record the analysis results of a biosample on a data storage medium such as a computer memory, disk drive, magnetic tape, or compact disk, which may include an identification tag to correlate the biosample with the analysis results.

High-performance computer data storage systems such as optical disc and magnetic tape libraries possess the automation to facilitate the scanning and analysis of biosamples, and to tabulate the resulting analysis data. For example, these systems may analyze the biosamples using magnetic tape read heads to detect magnetized nanoparticles attached to the biosamples. The biosamples and analysis data may be stored in different locations following the analysis, which make it difficult to correlate the biosamples with the corresponding data when needed. For a large number of biosamples and capillary tubes used to store the biosamples, the task of correlating the biosamples to their data becomes even more complex. It is desirable to exploit the use of automation functions available in data storage library systems to facilitate the correlation and management of biosample capillary tubes and biosample analysis data.

BRIEF SUMMARY OF THE DISCLOSURE

The disclosure relates to storage cartridges that include internal slots for holding biosample capillary tubes and have the same form factor as data cartridges to allow the biosample tube cartridges to be handled by the same robotic mechanisms that handle data cartridges in automated data storage library systems. One aspect of the disclosure concerns a cartridge comprising an enclosure that has a movable door to provide access to inside the enclosure. The enclosure includes a tube holder that has a plurality of cylindrical holes or longitudinal slots for receiving capillary tubes. The capillary tubes include biosamples that may be scanned and analyzed by the automated tape library.

Another aspect of the invention concerns an analytical system that comprises an automated tape library and a capillary tube storage cartridge. The capillary tube storage cartridge comprises an enclosure having a holder in the enclosure and a movable door to provide access to the holder. The enclosure has the same form factor as a data tape cartridge used in the automated tape library. The holder comprises a plurality of cylindrical holes or longitudinal slots for receiving the capillary tubes, wherein the capillary tubes contain biosamples that may be canned and analyzed by the automated tape library.

Still another aspect of the disclosure concerns an analytical system that comprises a tape drive and a capillary tube storage cartridge. The capillary tube storage cartridge comprises an enclosure having a holder in the enclosure and a movable door to provide access to the holder. The enclosure has the same form factor as a data tape cartridge used in the tape drive. The holder comprises a plurality of cylindrical holes or longitudinal slots for receiving the capillary tubes, wherein the capillary tubes contain biosamples that may be scanned and analyzed by the tape drive.

The details of the exemplary embodiments of the disclosure, both as to its structure and operation, are described below in the Detailed Description section in reference to the accompanying drawings. The Brief Summary is intended to identify key features of the claimed subject matter, but it is not intended to be used to limit the scope of the claimed subject matter.

DETAILED DESCRIPTION OF THE DISCLOSURE

Embodiments of the disclosure relate to a biosample capillary tube storage cartridge that includes internal cylindrical holes or longitudinal slots for holding biosample capillary tubes. The biosamples of the cartridge may be scanned and analyzed by the tape drives in an automated tape library. The cartridge may be handled by the robotic mechanisms of the library and stored in the cartridge storage slots of the library. The capillary tubes contain biological samples that may be written to by electromagnetic tape heads. The biosamples may then be scanned and read by anisotropic magneto-resistive (AMR), giant magnetoresistive (GMR) or tunnel magnetoresistive (TMR) read elements to detect the presence of target substances or micro-organisms in the biological samples. The capillary tube storage cartridge may have the same form factor as the magnetic tape cartridges used to store data and thus may be conveniently accessed, manipulated, and processed by robotic mechanisms in tape drives and tape libraries. The biosample storage cartridge may be handled through the same library internal-external mail slot as a tape cartridge. The same tape automation mechanisms and processes used in modern tape libraries may be employed for long-term biological-archival storage of the biosamples contained in the capillary tube storage cartridge.

The capillary tube storage cartridge may include a tube holder to retain the capillary tubes in the cartridge when the cartridge is moved, for example, by a robotic picker in a tape library as well as when the cartridge is in storage. The tube holder may have a plurality of cylindrical holes or longitudinal slots for receiving the biosample capillary tubes. Various exemplary embodiments of the capillary tube storage cartridge are described in detail below with reference to FIGS. 1-5.

Figure 1:
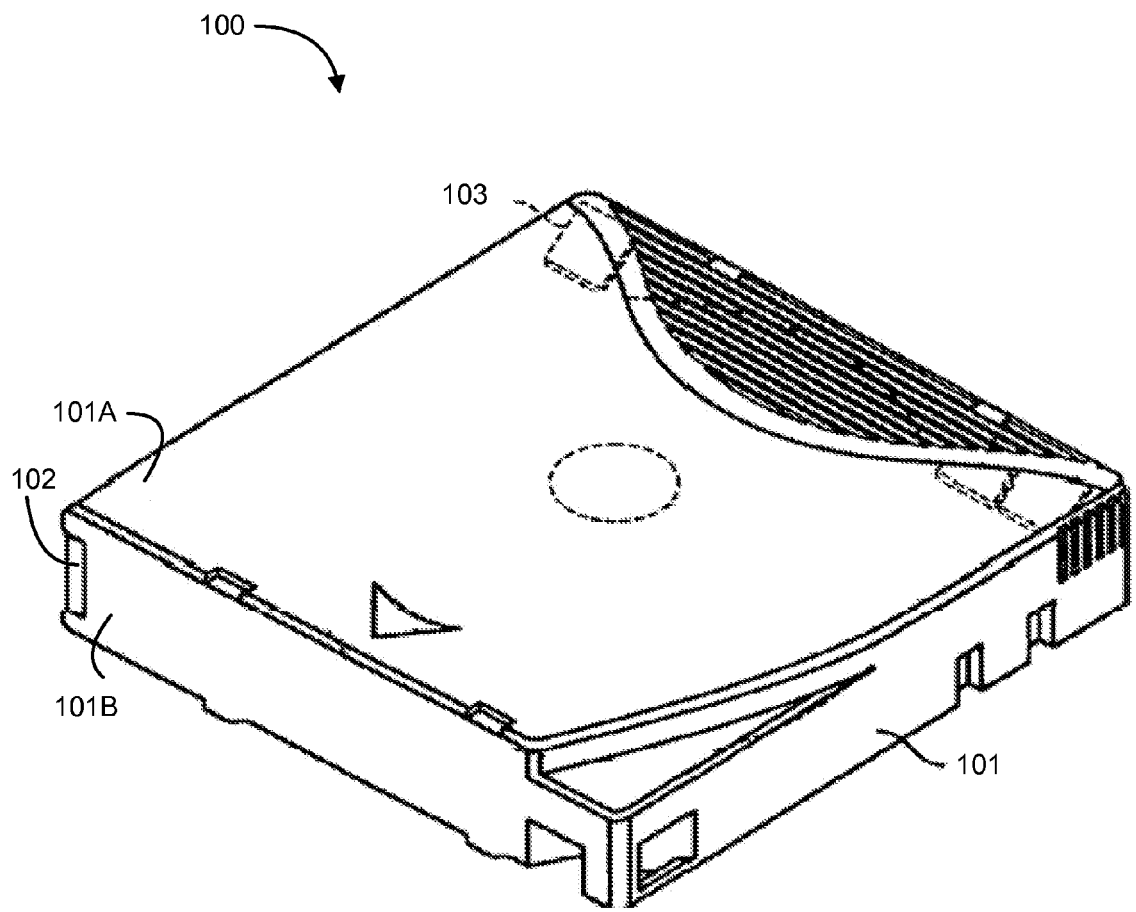
FIG. 1 illustrates an exemplary cartridge for storing biosample capillary tubes, in accordance with an embodiment of the invention.

Referring to the drawings and in particular to FIG. 1, there is illustrated an exemplary capillary tube storage cartridge 100 in which a plurality of cylindrical holes or longitudinal slots may be provided to hold biosample capillary tubes. The capillary tube storage cartridge 100 comprises an enclosure 101 which may include one or more parts. The cartridge 100 may have a movable side door 102 that can be slid open, for example by a tape drive, to gain access to the interior space of the cartridge 100. The tape drive may be adapted to perform biosample analysis. In one embodiment, the capillary tube storage cartridge 100 may comprise a top shell 101A and a bottom shell 101B wherein the top shell 101A is removably affixed to the bottom shell 101B by screws or other fasteners. Alternatively, the capillary tube storage cartridge 100 may have a front, top, or rear door that is movable to provide access to the biosample capillary tubes in the cartridge.

The capillary tube storage cartridge 100 may have the same size and exterior configuration as a magnetic tape storage cartridge based on LTO (Linear Tape Open) technology, the IBM TS1130 magnetic tape data storage cartridge, or the Oracle T10000 tape cartridge. In an alternate embodiment, older IBM single-reel tape cartridges could be used, such as the 3480, 3490, and 3590 tape cartridges. In a data storage cartridge, a data storage media such as a magnetic tape, may be mounted on a tape reel and occupy the space inside the capillary tube storage cartridge 100 rather than the biosample capillary tubes. Such a tape data storage cartridge may comprise a cartridge brake release button to allow the tape reel to freely rotate once the cartridge is loaded into a data storage drive.

The capillary tube storage cartridge 100 may further include one or more cartridge memories 103 for storing identification information about the storage cartridge 100, data related to the capillary tubes, and analysis data associated with the biosamples stored in the capillary tubes contained in the cartridge 100. Each cartridge memory 103 may comprise a transponder having a wireless interface, which is retained in the cartridge 100, for example, by being encapsulated by the cartridge when it is assembled. The encapsulation process is understood by those of skill in the art as applied to a single cartridge memory.

Figure 2:
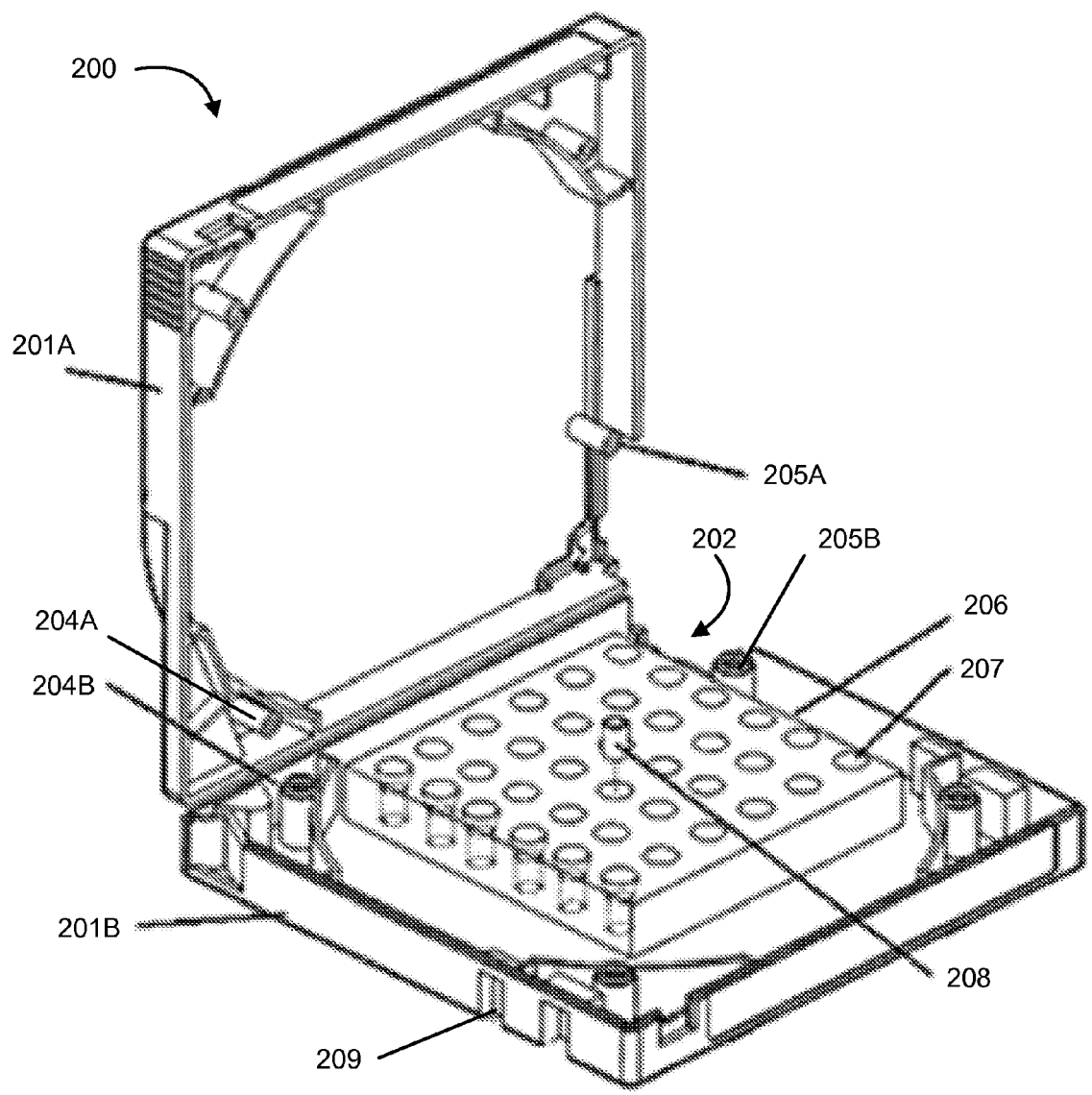
FIG. 2 illustrates a biosample storage cartridge with its cover opened to show vertical cylindrical holes for holding the biosample capillary tubes in the cartridge in a vertical position, in accordance with an embodiment of the invention.

FIG. 2 illustrates a capillary tube storage cartridge 200 with its top cover 201A opened to show the cylindrical holes for holding biosample capillary tubes, in accordance with an embodiment of the invention. The top cover 201A and bottom cover 201B may be held together by mating pins 204A-B, 205A-B and screws. The storage cartridge 200 comprises a tube holder 206 attached to bottom cover 201B for holding a plurality of capillary tubes 208. The tube holder 206 may be an integral part of the tube storage cartridge 200 or a separate part that is attached to the tube storage cartridge 200 by fasteners or adhesive. The tube holder 206 may comprise a plurality of cylindrical holes 207 to hold the capillary tubes 208 in a vertical position. The tube holder 206 prevents the capillary tubes 208 from being displaced when the storage cartridge 200 is being moved, for example by a robotic arm of a tape library system. The robotic arm may grasp the cartridge 200 at notches 209 in the cartridge cover 201B. The opening 202 normally covered by movable door 102 is shown near the upper right corner of the cartridge 200 to provide access to the capillary tubes 208.

In one embodiment, the diameter of the cylindrical holes 207 may be slightly larger than the diameter of the capillary tubes 208 to snugly accommodate the capillary tubes 208 and firmly retain the capillary tubes 208 in the cylindrical holes 207 by friction. In one embodiment, the capillary tubes 208 may have a diameter of 1.0 mm and the diameter of the cylindrical holes 207 is slightly larger than 1.0 mm, for example, 1.1 mm. In an alternate embodiment, the material containing cylindrical holes 207 is elastic, such as a polymer or elastomer, and the diameter of the cylindrical holes 207 is slightly smaller, ranging from 0.90 mm to 1.0 mm.

The inside and outside of the biosample storage cartridge 200 may have a coating of a thin nanocomposite film that comprises titanium dioxide and nitrogen to eradicate bacteria which might try to escape the cartridge 200. Titanium dioxide based coatings can eradicate bacteria after activation with UV light. The addition of nitrogen to these coatings enables photons available in visible light to be utilized to activate the surface and eradicate bacteria. Alternately, this coating may comprise nickel-alloy, copper-alloy, zinc oxide, or a film comprising silver particles in a fluoropolymer matrix enhanced by depositing an additional very thin layer of gold or brass clusters.

Figure 3:
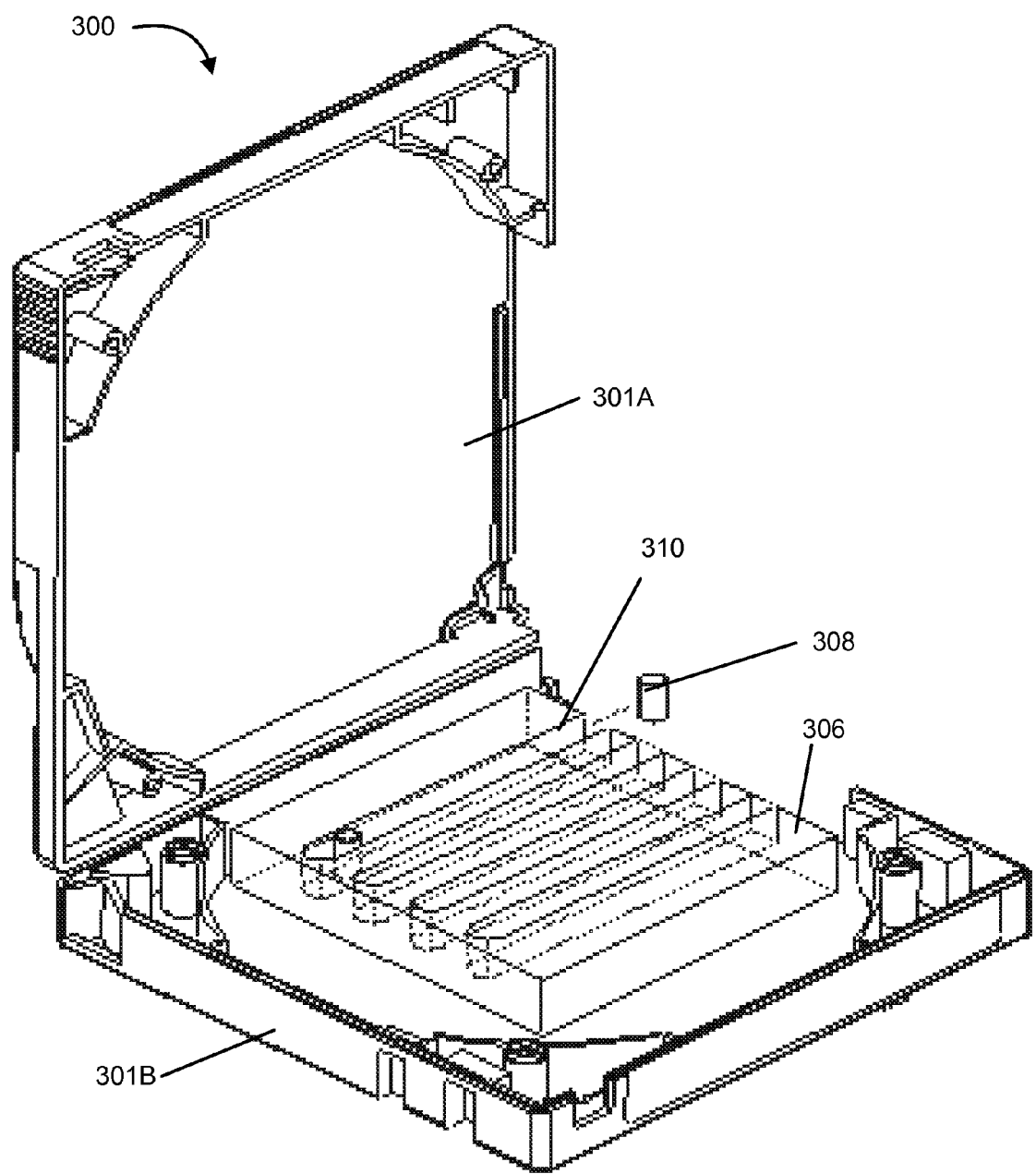
FIG. 3 illustrates a biosample storage cartridge with its cover opened to show longitudinal slots for holding the biosample capillary tubes in a vertical position, in accordance with an embodiment of the invention.

FIG. 3 illustrates an alternate embodiment of a biosample storage cartridge 300 with its cover opened to show longitudinal slots for holding the biosample capillary tubes in a vertical position, in accordance with an embodiment of the invention. The storage cartridge 300 may comprise a top cover 301A and a bottom cover 301B. A tube holder 306 may be disposed on the surface of bottom cover 301B, as shown, and includes longitudinal slots 310 for receiving the capillary tubes 308 in a vertical position. The width of the longitudinal slots 310 may be slightly larger than the diameter of the capillary tubes 308 to snugly retain the capillary tubes 308 in place, but at the same allow them to be inserted into and removed from the longitudinal slots 310.

Figure 4:
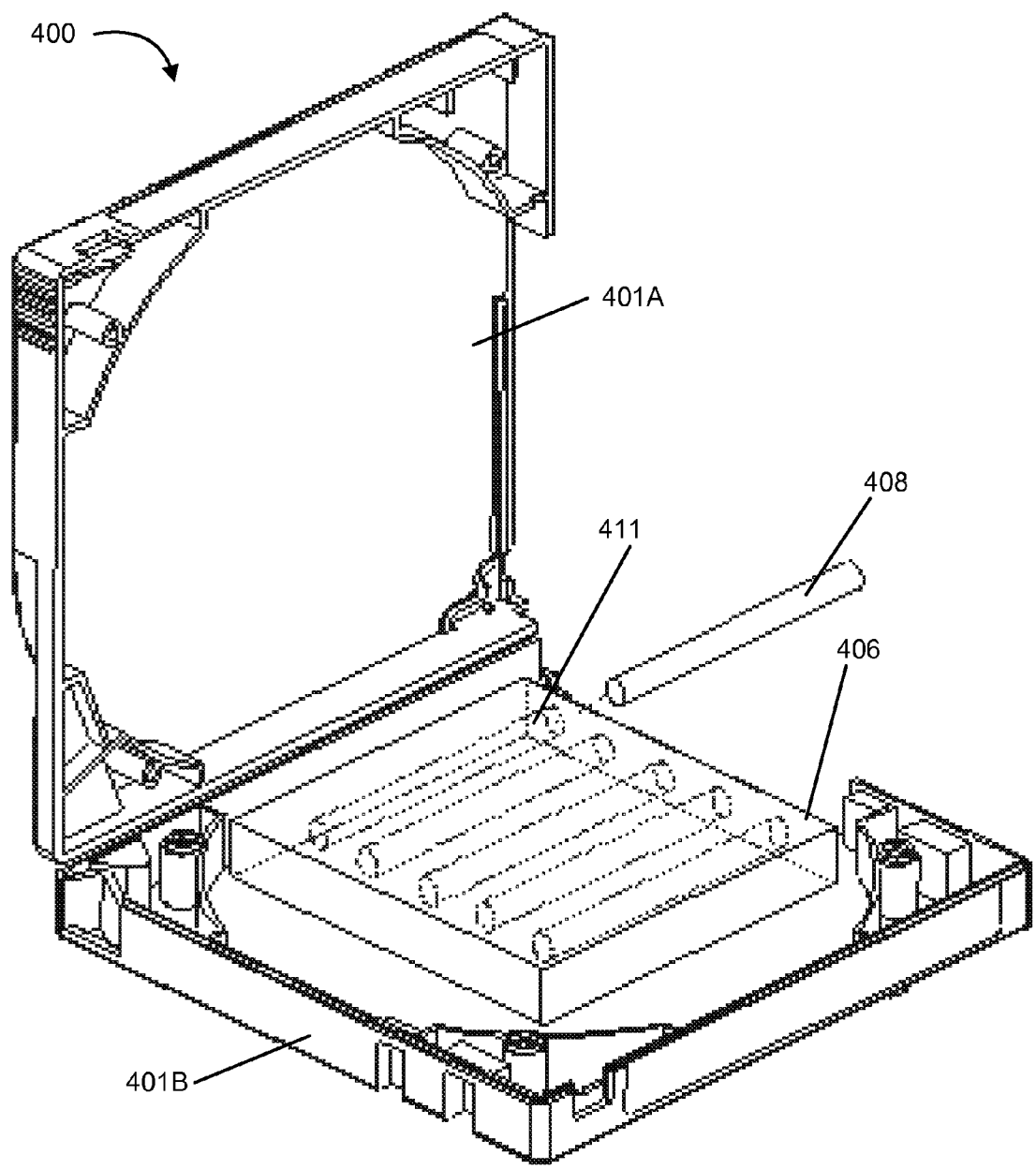
FIG. 4 illustrates a biosample storage cartridge with its cover opened to show horizontal cylindrical holes for holding the biosample capillary tubes in a horizontal position, in accordance with an embodiment of the invention.

FIG. 4 illustrates another embodiment of a biosample storage cartridge 400 with its cover opened to show horizontal cylindrical holes for holding the biosample capillary tubes in a horizontal position, in accordance with an embodiment of the invention. The storage cartridge 400 may comprise a top cover 401A and a bottom cover 401B. A tube holder 406 may be disposed on the surface of the bottom cover 401B, as shown, and includes cylindrical holes 411 for receiving the capillary tubes 408 in a horizontal position. The diameter of the cylindrical holes 411 may be slightly larger than the diameter of the capillary tubes 408 to snugly retain the capillary tubes 408 in place, but at the same allow them to be inserted into and removed from the cylindrical holes 411.

Figure 5:
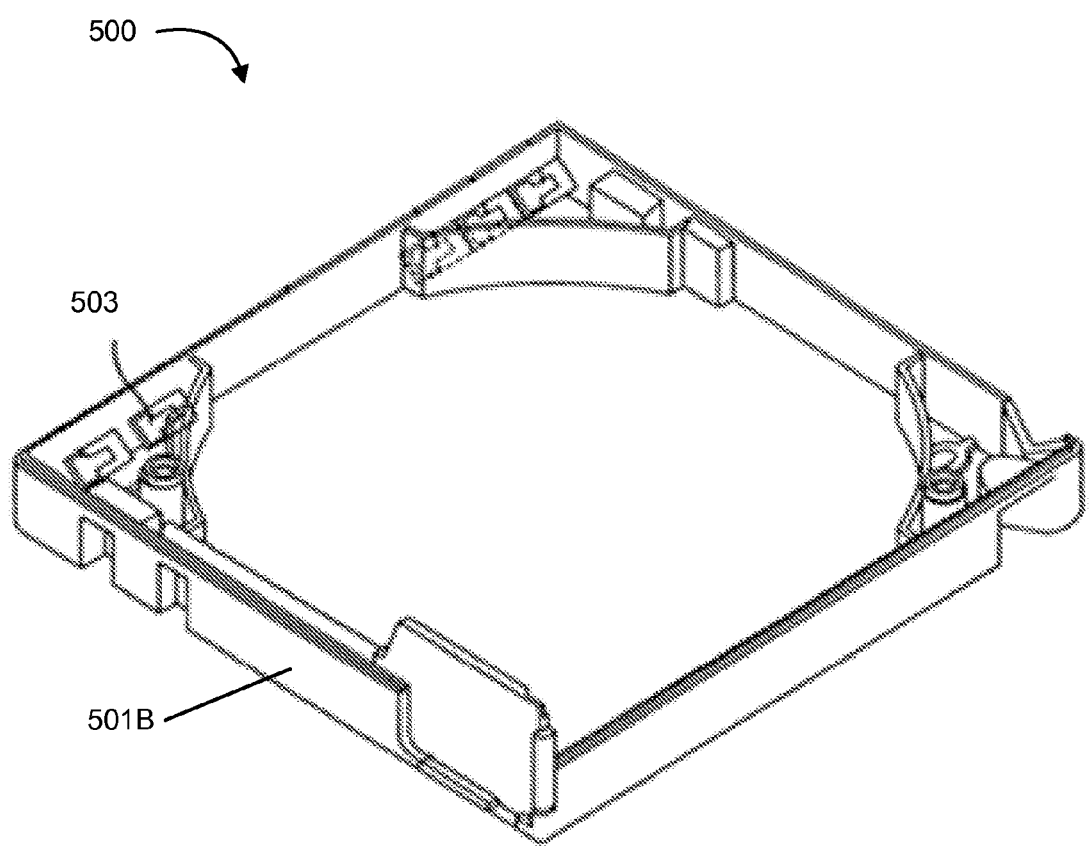
FIG. 5 illustrates a biosample storage cartridge with one or more memory components for storing and wirelessly transmitting information related to the cartridge, capillary tubes, biosamples, and biosample analysis, in accordance with an embodiment of the invention.

FIG. 5 illustrates a biosample storage cartridge 500, with bottom 501B containing one or more memory component 503 for storing information related to the biosample storage cartridge and its contents, for example, the identification of the cartridge, of the biological samples, of the capillary tubes, analysis data on the biological samples, and relevant dates such as creation dates and analysis dates. The cartridge memory 503 may be in communication with a wireless communication interface to send information to and receive information from a remote transceiver, for example, in a tape library system that handles the capillary tube storage cartridge 500.

Although FIGS. 1-5 illustrate the capillary tube storage cartridges that have the same form factor as a single reel magnetic tape cartridge, these capillary tube storage cartridges may have the same form factor as a dual reel cartridge, such as the IBM 3570 cartridge. In a dual reel cartridge, the magnetic tape is fed between the two reels of the cartridge. Such a capillary tube storage cartridge may comprise a capillary tube holder 206 in the space occupied by the two tape reels instead of the space occupied by a single tape reel, as described with reference to FIGS. 1-5.

Figure 6:
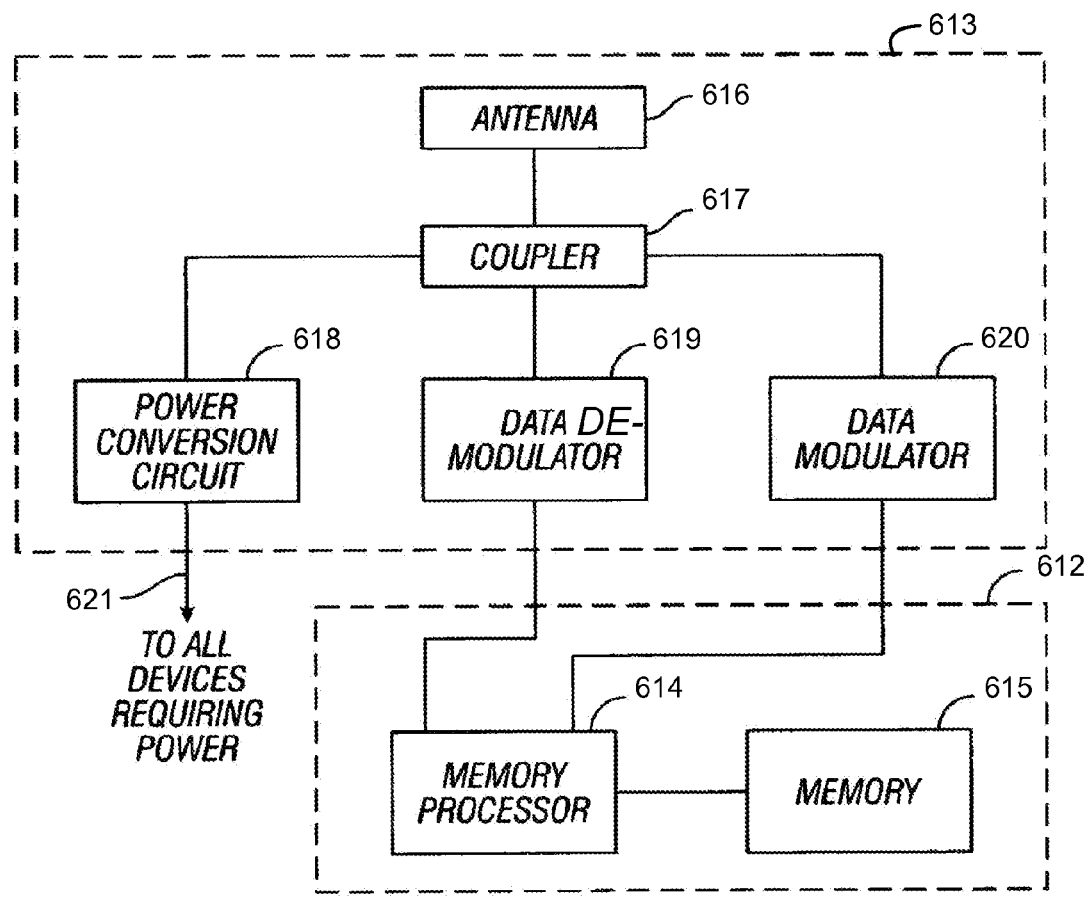
FIG. 6 illustrates a block diagram of a memory component and a wireless communication interface, which may be part of a capillary tube storage cartridge, for storing and transferring information related to the cartridge and its contents, in accordance with an embodiment of the invention.

FIG. 6 illustrates a block diagram of the functional components of a memory 612 and a wireless communication interface 613, which may be part of a cartridge memory 503 in a capillary tube storage cartridge 500. The memory component 612 may contain information about the biosample cartridge, capillary tubes stored in the cartridge, and biosamples in the capillary tubes. The memory component 612 may comprise a nonvolatile memory 615, such as an electrically erasable programmable read-only memory (EEPROM), a phase-change memory, flash memory, NOR memory, or a NAND memory arranged to operate in a low power environment.

Memory component 612 also may comprise memory processor 614, such as logic or a microprocessor chip, for example, an Intel Pentium™ chip arranged to operate in a low power environment, such as a portable computer. The memory processor 614 may have computer readable program code embodied therein, including suitable security and encryption/decryption algorithms, and the logic for accessing and operating the memory component 612. The nonvolatile storage 615 may comprise a separate chip attached to the logic or memory processor 614, or may comprise a portion of the same chip. The computer readable program code may be stored in a nonvolatile internal memory of the processor 614 or in the nonvolatile memory 615, and loaded into the processor 614. Alternatively, the memory component 612 may be operated by a control system or processor of an analytical system that uses the capillary tube storage cartridge 500.

In the illustrated embodiment, the wireless communication interface 613 may be a radio frequency (RF) wireless interface. An example of an RF wireless interface is described in U.S. Pat. No. 4,941,201. A high frequency inductive wireless interface may also be employed, which is of sufficiently high frequency so that it does not adversely affect magnetic storage media that may be present in a tape library system that handles the biosample storage cartridge. Examples of high frequency inductive wireless interfaces are described in U.S. Pat. No. 4,650,981, U.S. Pat. No. 4,758,836, and U.S. Pat. No. 3,859,624.

The wireless communication interface 613 includes an antenna 616 for receiving an RF signal from an RF interface of either a tape drive modified to perform bio-analysis or a robotic picker that moves the capillary tube storage cartridge 500 in a tape library system. The antenna 616 may be positioned at an angle in the range of 30-60 degrees for optimal reception of the RF signal, e.g., at 45 degrees as shown for the cartridge memory 503 of FIG. 3. The antenna 616 may be a quarter wave antenna, a fractal antenna, or the inductor of an inductor-capacitor oscillator.

A coupler 617 supplies the received signal to a power conversion circuit 618 and to a data demodulator 619. The power conversion circuit 618 converts the received signal to a power current, supplying the current on line 621 to all devices on the capillary tube storage cartridge 500, including the memory component 612, the data demodulator 619, and a data modulator 620. The received signal from antenna 616 may be encoded.

The data demodulator 619 receives the incoming coded signal from coupler 617 and demodulates the signal to provide data signals to the memory component 612 and for writing to memory 615. Data signals being read from memory 615 and memory component 612 are provided to the data modulator 620 which encodes the signals for transmission by coupler 617 and antenna 616 to an RF interface, which may be in either the robotic picker of the tape library system that handles the capillary tube storage cartridge 500 or in the tape drive modified to perform bio-analysis.

Figure 7:
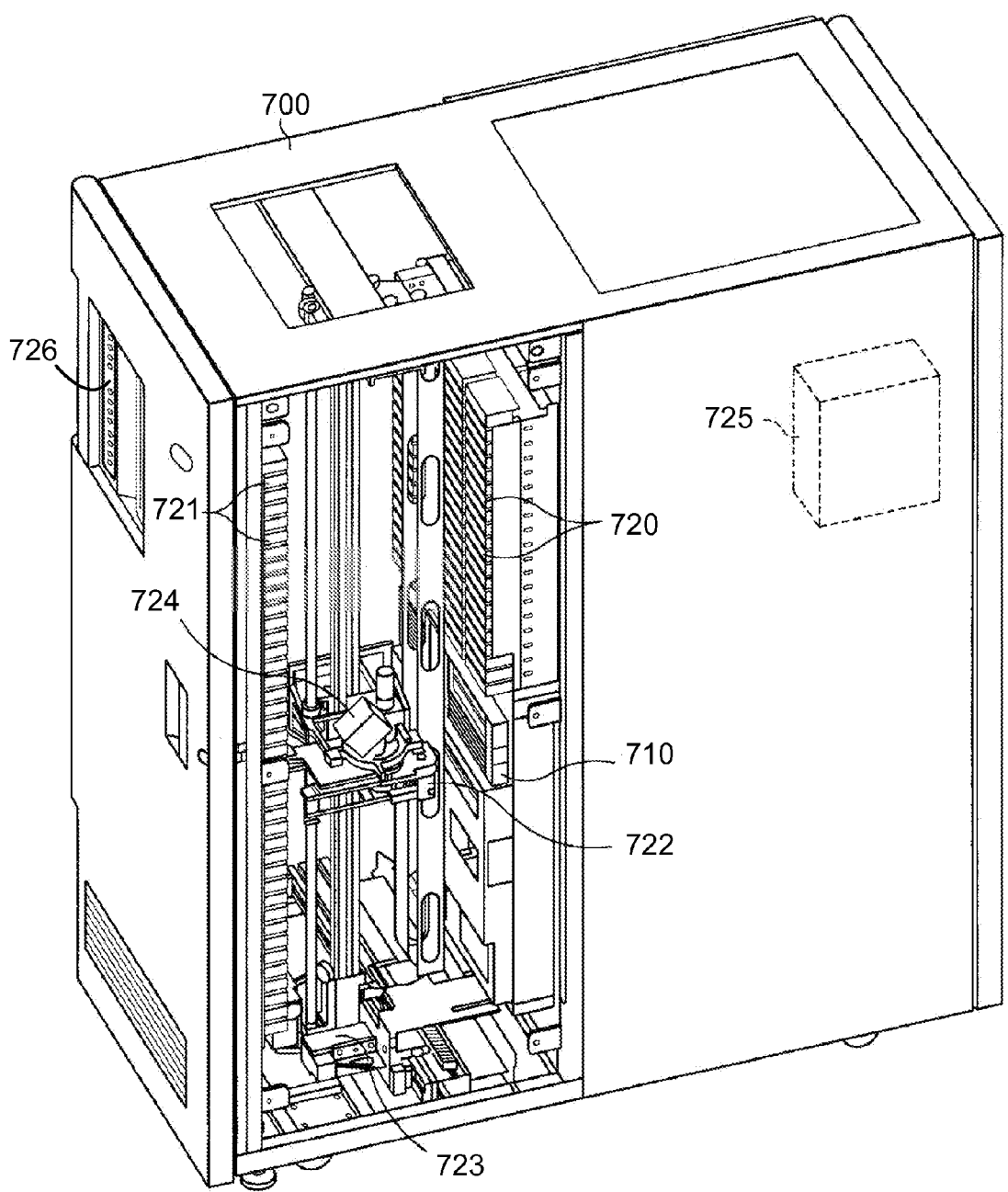
FIG. 7 illustrates an automated data storage tape library that may be used with the disclosed capillary tube storage cartridge, in accordance with an embodiment of the invention.

FIG. 7 illustrates an automated data storage tape library 700 that may be used with the capillary tube storage cartridge shown in FIGS. 1-6, in accordance with an embodiment of the invention. The data storage tape library 700 is an automated tape library that may include a number of tape drives 710 for reading and writing data on magnetic tape media, such as single-reel or two-reel magnetic tape cartridges. Examples of the library 700 include IBM TS3400™ and TS3500™ Tape Libraries, IBM TotalStorage™ 3494 Tape Libraries, and IBM 3952™ Tape Frames Model C20, which store magnetic tape cartridges and use IBM TS1130™ tape drives. Other examples of the library 700 include IBM TS3310™ and TS3100/3200™ tape libraries which store magnetic tape cartridges and use IBM LTO (Linear Tape Open) tape drives. Tape drives modified to perform bio-analysis accept cartridges 100, 200, 300, 400 and 500 from the robotic picker, withdraw a biosample capillary tube through a cartridge door, e.g., door 102 of cartridge 100, and perform the bio-analysis.

A plurality of cartridges 720 are stored in banks or groups of cartridge storage slots 721. Cartridges 720 may comprise tape media for data storage, tape substrate for biosamples, or biosample capillary tubes 208, 308 and 408 for bio-analysis. Tape media may encompass a variety of media, such as that contained in magnetic tape cartridges, magnetic tape cassettes, and optical tape cartridges, in various formats. For universal reference to any of these types of media, the terms "tape media" or "media" are used herein, and any of these types of containers are referred to as "tape cartridges" or "cartridges" herein. An access robot 723, including a cartridge picker 722 and a bar code reader 724 mounted on the cartridge picker 722, transports a selected cartridge 720 between a cartridge storage slot 721 and a drive 710. Bar code reader 724 is mounted directly on picker 722 so that the library 700 can check the bar code on cartridge 720 before picking the cartridge and transporting it to a drive 710, storage slot 721, or import/export mail slot 726.

The automated tape library 700 further has a library controller 725 which includes at least one microprocessor. The library controller 725 may serve to provide an inventory of the cartridges 720 and to control the library 700. Typically, the library controller 725 has suitable memory and data storage capability to control the operation of the library 700. The library controller 725 controls the actions of the access robot 723, cartridge picker 722, and bar code reader 724. Barcode reader 724 may read a barcode from a cartridge such as cartridge 200.

The library controller 725 is interconnected through an interface to one or more host processors, which provides commands requesting access to a particular biosample capillary tube, a tape media, or a cartridge in particular cartridge storage slots. A host, either directly or through the library controller, controls the actions of the drives 710 which either perform data IO with tape media or, if suitably modified, perform bio-analysis on biosamples extracted from the capillary tubes. Commands for accessing data or locations on the tape media and biosample capillary tubes, and information to be recorded on or to be read from selected tape media and biosample capillary tubes, are transmitted between the drives 710 and the host. The library controller 725 is typically provided with a database for locating the cartridges 720 in the appropriate storage slots 721 and for maintaining the cartridge inventory.

Library 700 also includes an import/export mail slot 726, which is a portal allowing cartridges 720 to be entered into or removed from library 700. Since cartridges 720 have a generally identical exterior dimensions regardless of whether they hold data tape or biosample tubes, cartridges 720 may enter library 700 through import/export mail slot 726, picked up by picker 722 and transported to either cartridge-storage slot 721 or drives 710. Drives 710 would have a common cartridge loader mechanism, whether the drive is a data drive or a bio-analysis drive, because of cartridges 720 having identical exterior dimensions. Similarly, picker 722 may pick a cartridge 720 from a drive 710 or cartridge-storage slot 721 and place it in import/export mail slot 726 for removal from library 700. In an alternate embodiment, biosample cartridges 720 are a different color from cartridges containing digital data, as well as containing information regarding their intended purpose in memories 503.

Figure 8:
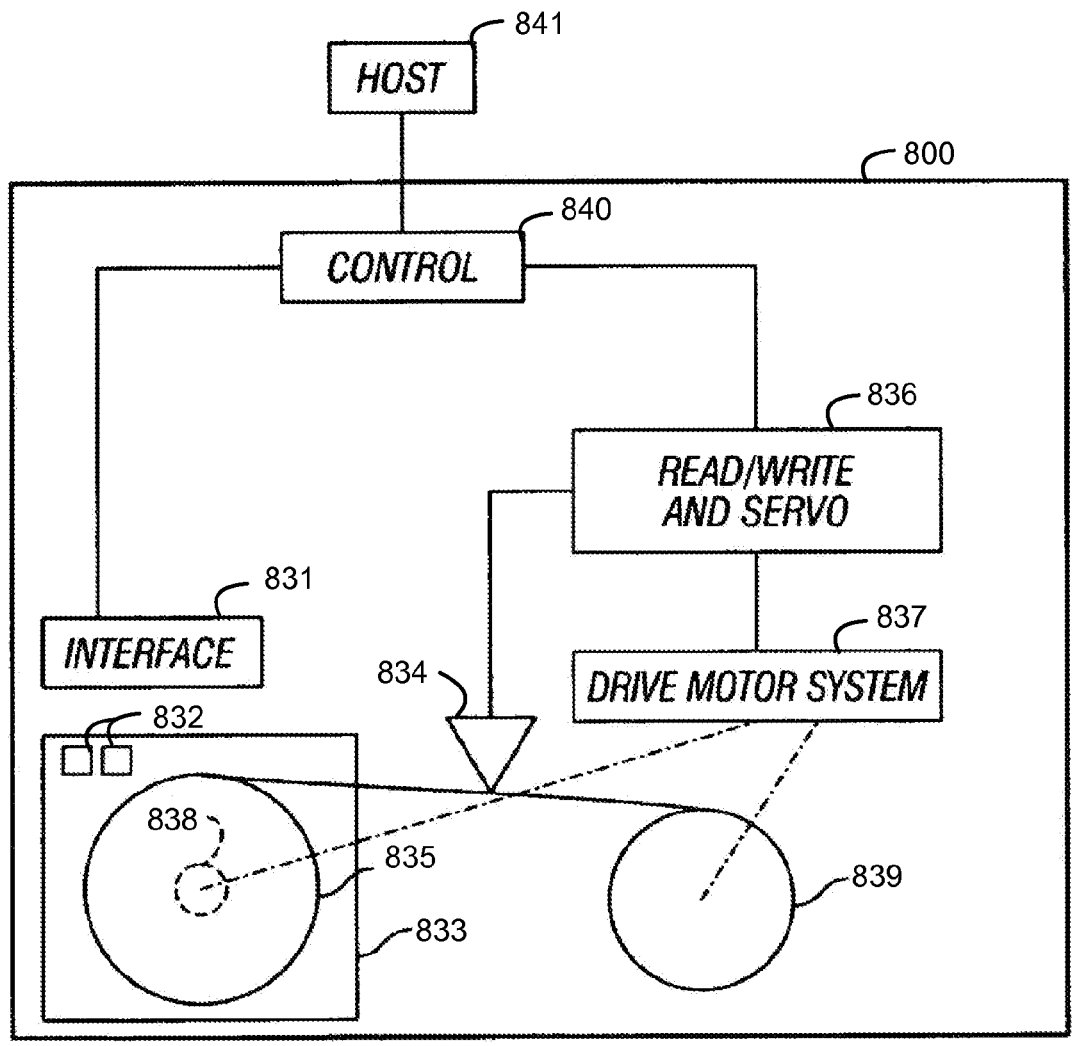
FIG. 8 illustrates a block diagram of the main functional components in a data storage tape drive that may be used for analyzing a biosample and storing biosample identification and analysis data, in accordance with an embodiment of the invention.

FIG. 8 illustrates a block diagram of the functional components in a tape drive that may be used for analyzing a biosample and storing biosample identification and analysis data, in accordance with an embodiment of the invention. The magnetic tape drive 800 comprises a memory interface 831 for reading information from and writing information to one or more of the cartridge memories 832 of the magnetic tape cartridge 833, for example, in a contactless manner.

A read/write system is provided for reading and writing information to the data storage media, such as magnetic tape, or nanoparticles attached to the biosamples, and may comprise a read/write head 834 with a servo system for moving the head laterally of the magnetic tape 835 or a biosample plate. The servo system may comprise a read/write and servo control 836 and a drive motor system 837 which moves the magnetic tape 835 between the cartridge reel 838 and the take up reel 839 and across the read/write head 834. The read/write and servo control 836 controls the operation of the drive motor system 837 to move the magnetic tape 835 across the read/write head 834 at a desired velocity. The read/write and servo control 836 may determine the location of the read/write head 834 with respect to the magnetic tape 835.

In one example, the read/write head 834 and read/write and servo control 836 employ servo signals on the magnetic tape 835 to determine the location of the read/write head 834, and in another example, the read/write and servo control 836 employs at least one of the reels, such as by means of a tachometer, to determine the location of the read/write head 834 with respect to the magnetic tape 835. The read/write head 834 and read/write and servo control 836 may comprise hardware elements and may comprise any suitable form of logic, including a processor operated by software, or microcode, or firmware, or may comprise hardware logic, or a combination.

A control system 840 communicates with the memory interface 831, and communicates with the read/write system, e.g., at read/write and servo control 836. The control system 840 may comprise any suitable form of logic, including a processor operated by software, or microcode, or firmware, or may comprise hardware logic, or a combination thereof. The control system 840 typically communicates with one or more host systems 841, and operates the data storage drive 800 in accordance with commands originating at a host. Alternatively, the data storage drive 800 may form part of a subsystem, such as a library, and may also receive and respond to commands from the subsystem.

As illustrated, the data storage drive 800 provides information to a cartridge memory 832 of the magnetic tape cartridge 833, and provides data to the magnetic tape 835 of the magnetic tape cartridge 833.

In one embodiment, the data storage tape drive 800 may function as an analytical system for scanning the biosample capillary tubes 208, 308, 408 and analyzing biological samples stored in the capillary tubes 208, 308 and 408 to detect the presence of target antigens or substances. The magneto-resistive (MR) heads of the read/write head 834 in data storage drive 800 may act as the scanners for reading data from the biosamples. Write heads of read/write head 834 may magnetize nanoparticles used to tag the biosamples which are subsequently read or detected by the MR heads. For example, an MR read/write head 834 may be used to detect microorganisms and antigens that are attached to magnetized nanoparticles.

An MR read-write head may scan a large number of biosamples deposited on a magnetic tape media as the MR read-write head traverses the tape media a high speed. The tape drive electronics may then process the signals from the read-write MR head to detect the presence of target micro-organisms or antigens in the biosamples. Such as bio-assay process is described, for example, in the commonly-assigned U.S. patent application entitled "Detection Of Analytes Via Nanoparticle-Labeled Substances With Electromagnetic Read-Write Heads", Ser. No. 12/888,388, herein incorporated by reference in its entirety.

Figure 9:
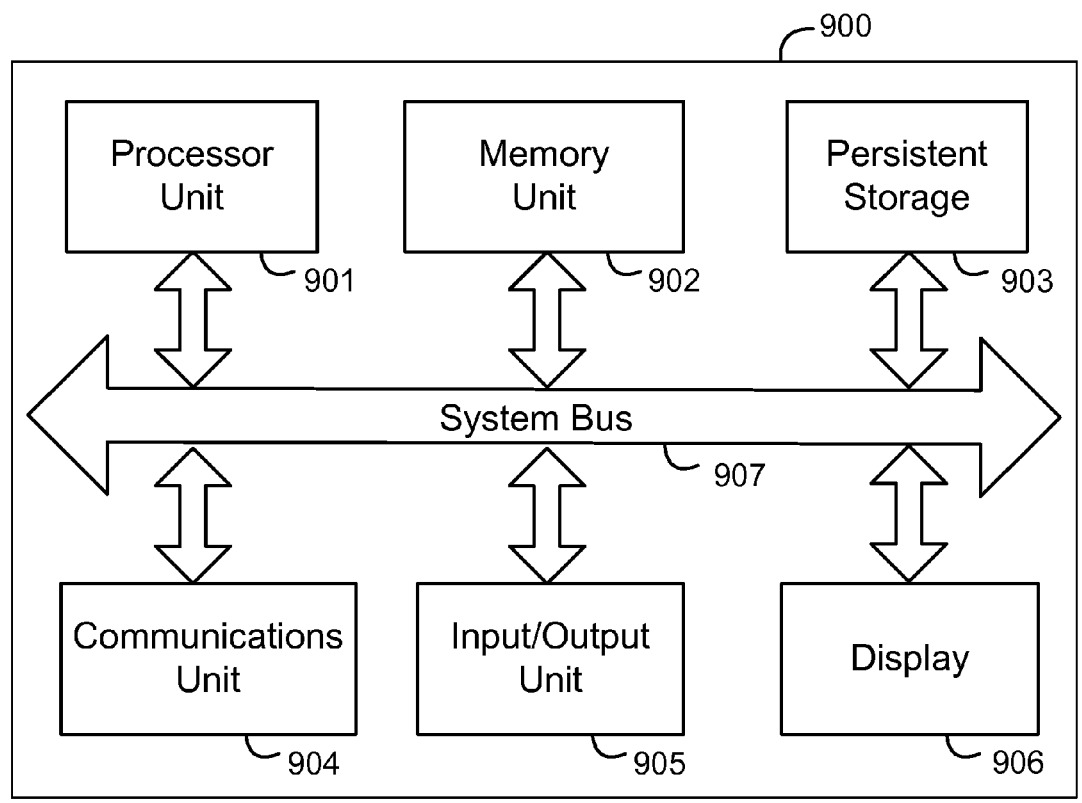
FIG. 9 illustrates a block diagram of the functional components in a computer, which may be incorporated into a data storage tape library and a cartridge memory to provide control and processing functions, in accordance with an embodiment of the invention.

FIG. 9 illustrates a block diagram of a representative computer system, some of which may be incorporated in a data storage tape library and a cartridge memory to provide control and processing function, for providing aspects of the disclosure. Computer system 900 includes a processor 901, a memory 902, a persistent storage 903, a communication interface 904, an input/output unit 905, a display 906 and a system bus 907. Computer programs are typically stored in persistent storage 903 until they are needed for execution by an operating system running in memory 902. Persistent storage 903 may comprise one or more hard disk drives and multiple hard disk drives may be organized into a RAID, CD (Compact Disk) drives, DVD (Digital Versatile Disk) drives, BD (Blu-Ray) drives, SSD (Solid State Drives), and solid state memory. At that time, the programs are brought into the memory 902 so that they can be directly accessed by the processor 901. The processor 901 selects a part of memory 902 to read and/or write by using an address that the processor 901 gives to memory 902 along with a request to read and/or write. Usually, the reading and interpretation of an encoded instruction at an address causes the processor 901 to fetch a subsequent instruction, either at a subsequent address or some other address. The processor 901, memory 902, persistent storage 903, communication interface 904, input/output unit 905, and display 906 interface with each other through the system bus 907.

The subject matter described above is provided by way of illustration only and should not be construed as limiting. Various modifications and substitutions of the described components and operations can be made by those skilled in the art without departing from the spirit and scope of the present disclosure defined in the following claims, the scope of which is to be accorded the broadest interpretation so as to encompass such modifications and equivalent structures. For example, capillary tubes may be replaced by nanotubes, without loss of generality.

What is claimed is:

1. A cartridge for storing capillary tubes, comprising:
an enclosure including a movable door to provide access to inside the enclosure, the enclosure having the same form factor as a data tape cartridge used in an automated tape library;
a holder disposed in the enclosure and having a plurality of cylindrical holes for receiving a plurality of said capillary tubes, the capillary tubes being configured to house biosamples that are scanned and analyzed by the automated tape library; and
one or more memory modules coupled to the enclosure, each memory module being configured to store data relating to the biosamples, the capillary tubes, and the cartridge, wherein at least one of the one or more memory modules comprises a nonvolatile memory.

2. The cartridge of claim 1, wherein the cartridge is an LTO type cartridge.

3. The cartridge of claim 1, wherein diameters of the cylindrical holes are slightly larger than diameters of the capillary tubes to allow the holder to retain the capillary tubes in place when moving.

4. The cartridge of claim 1, further comprising at least two of the memory modules.

5. The cartridge of claim 4, further comprising a wireless communication interface coupled to the memory modules for sending data to and receiving data from the automated tape library.

6. The cartridge of claim 5, wherein the wireless communication interface uses radio signals for communication.

7. The cartridge of claim 6, wherein the wireless communication interface is a radio antenna selected from the group consisting of a quarter-wave antenna, a fractal antenna, and an inductor of an inductor-capacitor oscillator.

8. The cartridge of claim 1, wherein the nonvolatile memory is selected from a group consisting of electrically-eraseable programmable read-only memory, phase change memory, flash memory, NOR memory and NAND memory.

9. The cartridge of claim 1, further comprising the plurality of capillary tubes.

10. A cartridge for storing capillary tubes, comprising:
an enclosure including a movable door to provide access to inside the enclosure, the enclosure having the same form factor as a data tape cartridge used in an automated tape library;
a holder disposed in the enclosure and having a plurality of cylindrical holes for receiving a plurality of said capillary tubes, the capillary tubes being configured to house biosamples that are scanned and analyzed by the automated tape library; and
a plurality of memory modules for storing data related to the biosamples, capillary tubes and cartridge, and
wherein the memory modules comprise a nonvolatile memory selected from the group consisting of electrically-erasable programmable read-only memory, phase-change memory, flash memory, NOR memory, and NAND memory.

11. An analytical system comprising:
an automated tape library;
a cartridge comprising an enclosure having a holder inside the enclosure and a movable door to provide access to the holder, the enclosure having the same form factor as a data tape cartridge used in the automated tape library, the holder comprising a plurality of cylindrical holes for receiving a plurality of capillary tubes, and the capillary tubes being configured to house biosamples that are scanned and analyzed by the automated tape library; and
one or more memory modules disposed in the enclosure, each memory module being configured to store data relating to the biosamples, the capillary tubes, and the cartridge, wherein at least one of the one or more memory modules comprises a nonvolatile memory.

12. The analytical system of claim 11, wherein the cartridge is an LTO type cartridge.

13. The analytical system of claim 11, wherein the one or more memory modules are configured to store data related to the biosamples, the capillary tubes and the cartridge.

14. The analytical system of claim 13, wherein the cartridge comprises a wireless communication interface coupled to the at least one memory module for sending data to and receiving data from the automated tape library.

15. The analytical system of claim 14, wherein the wireless communication interface is a radio antenna selected from the group consisting of a quarter-wave antenna, a fractal antenna, and an inductor of an inductor-capacitor oscillator.

16. The analytical system of claim 13, at least one of the one or more memory modules comprising a nonvolatile memory selected from a group consisting of electrically-eraseable programmable read-only memory, phase change memory, flash memory, NOR memory and NAND memory.

17. An analytical system comprising:
a tape drive;
a cartridge comprising an enclosure having a holder inside the enclosure and a movable door to provide access to the holder, the enclosure having the same form factor as a data tape cartridge used in the tape drive, the holder comprising a plurality of cylindrical holes for receiving a plurality of capillary tubes, and the capillary tubes being configured to house biosamples that are scanned and analyzed by the tape drive; and
at least one memory module disposed in the enclosure, the at least one memory module comprising a nonvolatile memory selected from a group consisting of electrically-eraseable programmable read-only memory, phase change memory, flash memory, NOR memory and NAND memory.

18. The analytical system of claim 17, wherein the cartridge comprises a plurality of the memory modules, and wherein the memory modules are configured for storing data related to the biosamples, the capillary tubes and the cartridge.

19. The analytical system of claim 18, wherein the cartridge comprises a wireless communication interface coupled to the memory modules for sending data to and receiving data from the tape drive.

* * * * *